United States Patent [19]
McGill, III et al.

[11] Patent Number: 6,090,949
[45] Date of Patent: Jul. 18, 2000

[54] PROCESSES FOR PREPARING BENZOTHIOPHENES

[75] Inventors: John McNeill McGill, III, Lafayette; Jerry Wayne Misner; Tony Yantao Zhang, both of Indianapolis, all of Ind.

[73] Assignee: Eli Lilly and Company, Indianapolis, Ind.

[21] Appl. No.: 09/069,497

[22] Filed: Apr. 29, 1998

Related U.S. Application Data

[60] Provisional application No. 60/045,177, Apr. 30, 1997.

[51] Int. Cl.[7] .................. C07D 303/56; C07D 409/12
[52] U.S. Cl. .................. 549/51; 546/202; 548/525; 544/146; 540/596
[58] Field of Search .................................................. 549/51

[56] References Cited

U.S. PATENT DOCUMENTS

| | | |
|---|---|---|
| 3,394,125 | 7/1968 | Crenshaw . |
| 3,413,305 | 11/1968 | Crenshaw . |
| 4,133,814 | 1/1979 | Jones et al. ............................. 260/326 |
| 4,358,593 | 11/1982 | Jones et al. ............................. 546/202 |
| 4,380,635 | 4/1983 | Peters ..................................... 546/202 |
| 4,418,068 | 11/1983 | Jones et al. ............................. 424/267 |
| 5,223,510 | 6/1993 | Gubin et al. ............................ 514/299 |
| 5,395,842 | 3/1995 | Labrie et al. ........................... 514/320 |
| 5,470,854 | 11/1995 | Angerer et al. ......................... 514/233 |
| 5,472,962 | 12/1995 | Sagamihara et al. ................ 514/233.5 |
| 5,482,949 | 1/1996 | Black et al. ............................. 514/324 |
| 5,552,412 | 9/1996 | Cameron et al. ....................... 514/317 |
| 5,629,425 | 5/1997 | Labell et al. ............................ 546/202 |

FOREIGN PATENT DOCUMENTS

| | | |
|---|---|---|
| 0062503 | 10/1982 | European Pat. Off. . |
| 0062504 | 10/1982 | European Pat. Off. . |
| 0 605 193 | 7/1994 | European Pat. Off. . |
| 2097392 | 4/1982 | United Kingdom . |
| 2096608 | 10/1982 | United Kingdom . |
| 2097788 | 11/1982 | United Kingdom . |
| WO93/10741 | 6/1993 | WIPO . |
| WO95/10513 | 4/1995 | WIPO . |

OTHER PUBLICATIONS

Jones, C.D., et al, *J. Med. Chem.* 27(8)1057–1066 (1971).
Romeo Wagner, *Synthetic Organic Chemistry*, (171–172), (1953).
Jones, C.D., et al *J. Med. Chem.* 35(5) 931–938, 1992.
Kym, R.P. et al, *J. Med. Chem.,* ∓(24), 3911–3921.
Jackson, T.G., et al *J. Chem. Soc.* 1728–1729 (1969).
Kametani, et al *J. Org. Chem.* 41 (15) 2545–2547 1976.
Crenshaw, R.R., et al *J. Med. Chem.* 14(12) 1185–1190 (1971).

*Primary Examiner*—Bernard Dentz
*Attorney, Agent, or Firm*—Gilbert T. Voy

[57] ABSTRACT

The present invention relates to intermediates and processes for preparing benzothiophenes.

11 Claims, No Drawings

PROCESSES FOR PREPARING BENZOTHIOPHENES

CROSS-REFERENCE TO RELATED APPLICATIONS

This application claims priority to provisional application Ser. No. 60/045,177, filed Apr. 30, 1997.

BACKGROUND OF THE INVENTION

The present invention relates to the field of pharmaceutical chemistry and relates to intermediates and processes for preparing benzothiophenes.

Compounds of formula I

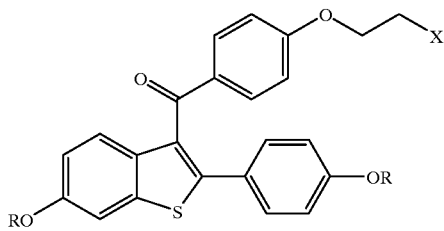

wherein R is —$COR^3$ or —$SO_2R^3$, X is chloro, bromo, or $SO_2R^3$, and $R^3$ is $C_1$–$C_4$ alkyl, trifluoromethyl, trichloromethyl, phenyl, p-tolyl, p-anisyl, or mono- or di(halo or nitro)phenyl may be prepared as described U.S. Pat. No. 4,358,593, the disclosure of which is herein incorporated by reference. That patent teaches an acylation reaction in which a compound of formula III

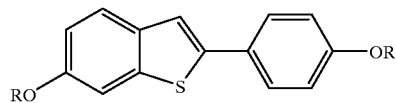

wherein R is, in both instances, a hydroxy protecting group, is reacted with a compound of formula IV

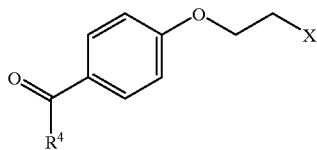

wherein $R^4$ is chloro, bromo, iodo, or an acyl activating group, under Friedel-Crafts acylation conditions, to provide a compound of formula I. If a compound of formula I where R is hydrogen is desired, this process requires two separate reactions and purifications- one for the acylation reaction, described above, and one for the deprotection reaction at the 4' and 6 positions.

Thus, a more efficient and less expensive process for preparing compounds of formula I would be a significant contribution to the art.

SUMMARY OF THE INVENTION

The present invention relates to a process for preparing a compound of formula VII

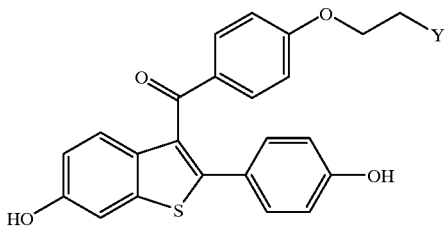

wherein Y is chloro, bromo, iodo, or $SO_2R^9$, and $R^9$ is $C_1$–$C_4$ alkyl, trifluoromethyl, trichloromethyl, phenyl, p-tolyl, p-anisyl, or mono- or di(halo or nitro)phenyl; which includes reacting a compound of formula V

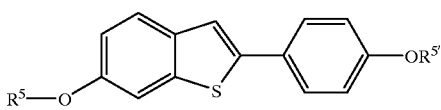

wherein $R^5$ and $R^{5'}$ are independently hydroxy protecting groups, with a compound of formula VI

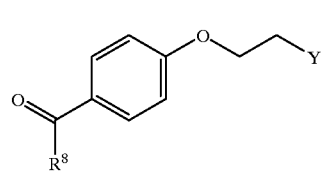

wherein $R^8$ is an acyl activating group, in the presence of a boron trihalide.

DETAILED DESCRIPTION

The present invention further relates to compounds of formula VII

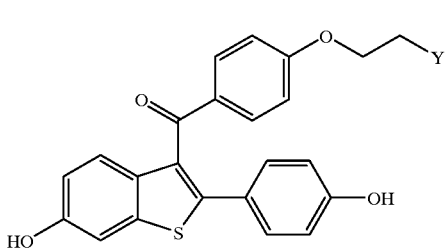

wherein Y is chloro, bromo, iodo, or $SO_2R^9$, and $R^9$ is $C_1$–$C_4$ alkyl, trifluoromethyl, trichloromethyl, phenyl, p-tolyl, p-anisyl, or mono- or di(halo or nitro)phenyl.

The present invention further relates to a process for preparing a compound of formula IX

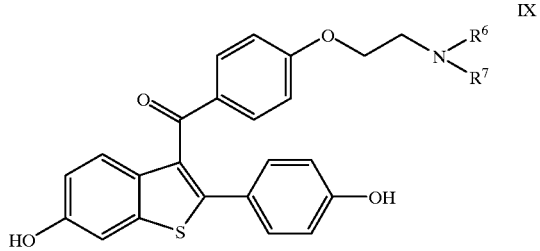

wherein $R^6$ and $R^7$ are independently $C_1$–$C_4$ alkyl, or combine together with the nitrogen to which they are attached to form a piperidinyl, pyrrolidinyl, methylpyrrolidinyl, dimethylpyrrolidinyl, morpholino, or 1-hexamethyleneimino ring; or a pharmaceutically acceptable salt or solvate, which includes reacting a compound of formula VII with a compound of formula VIII

wherein $R^6$ and $R^7$ are as defined above.

General terms used in the description of chemical formulas bear their usual meanings. For example, the term "$C_1$–$C_4$ alkyl" refers to straight or branched chains of 1 to 4 carbon atoms including, methyl, ethyl, propyl, isopropyl, butyl, n-butyl, isobutyl, and t-butyl; and the term "alkyl" encompasses the groups included in the definition of "$C_1$–$C_4$ alkyl" in addition to groups such as pentyl, 2-methylbutyl, isopentyl, hexyl, 2-methylpentyl, 3-methylpentyl, and the like. The term "lower alcohols" refers to $C_1$–$C_4$ alcohols including methanol, ethanol, propanol, isopropanol, butanol, n-butanol, isobutanol, and t-butanol.

The term "halo" includes bromo, chloro, fluoro, and iodo. The term "trihalide" refers to tribromide or trichloride.

The term "hydroxy protecting group" denotes a group understood by one skilled in the organic chemical arts of the type described in Chapter 2 of "Protective Groups in Organic Synthesis, 2nd Edition, T. H. Greene, et al., John Wiley & Sons, New York, 1991, hereafter referred to as "Greene". Such groups include, for example, ether groups including methyl and substituted methyl ether groups such as methyl ether, methoxymethyl ether, methylthiomethyl ether, tert-buylthiomethyl ether, (phenyldimethylsilyl) methoxymethyl ether, benzyloxymethyl ether, p-methoxybenzyloxymethyl ether, and tert-butoxymethyl ether; substituted ethyl ether groups such as ethoxyethyl ether, 1-(2-chloroethoxy)ethyl ether, 2,2,2-trichloroethoxymethyl ether, and 2-(trimethylsilyl)ethyl ether; phenyl and substituted phenyl ether groups such as phenyl ether, p-chlorophenyl ether, p-methoxyphenyl ether, and 2,4-dinitrophenyl ether; benzyl and substituted benzyl ether groups such as benzyl ether, p-methoxybenzyl ether, o-nitrobenzyl ether, and 2,6-dichlorobenzyl ether; and alkylsilyl ether groups such as trimethyl- triethyl- and triisopropylsilyl ethers, mixed alkyl-silyl ether groups such as dimethylisopropylsilyl ether, and diethylisopropylsilyl ether; and ester protecting groups of the general formula —CO—($C_1$–$C_6$) alkyl or —CO—Ar, where Ar is optionally substituted phenyl, or specific groups such as formate ester, benzylformate ester, mono- di- and trichloroacetate esters, phenoxyacetate ester, and p-chlorophenoxyacetate and the like. The species of hydroxy protecting group employed is not critical so long as the derivatized hydroxy group is stable to the condition of subsequent reaction(s) on other positions of the intermediate molecule and can be selectively removed at the appropriate point without disrupting the remainder of the molecule including any other hydroxy protecting group(s). Preferred protecting groups encompassed in this invention are methyl groups, for example, when $R^5$ or $R^{5'}$ at each occurrence is methyl.

The term "acyl activating group" refers to a substituent to a carbonyl that promotes nucleophilic addition reactions to the carbonyl. Suitable activating substituents are those which have a net electron withdrawing effect on the carbonyl. Typical electron withdrawing groups include groups that when combined with the carbonyl form an ester or amide. Such groups include hydroxybenzotriazole, imidazole, a nitrophenol, pentachlorophenol, N-hydroxysuccinimide, dicyclohexylcarbodiimide, N-hydroxy-N-methoxyamine, and the like. The term acyl activating group also encompasses groups that when combined with the carbonyl form an acid anhydride. Such groups include small carboxylic acids, such as acetic, formic, sulfonic, methanesulfonic, ethanesulfonic, benzenesulfonic, or p-tolylsulfonic acid, and the like. Furthermore, a halogen attached to carbonyl activates the carbonyl for nucleophilic addition. Suitable halogens include chloro, bromo, or iodo.

The term "suitable base" refers to any base reactive enough to effect the desired reaction without significantly effecting any undesired reactions.

The term "suitable solvent" refers to any solvent inert to the ongoing reaction that sufficiently solubilizes the reactants to effect the desired reaction.

The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, γ-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula IX with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula IX and a pharmaceutically acceptable diluent or carrier.

The starting materials for the processes of the present invention, including compounds of formula V, may be obtained by a number of routes, including those disclosed in U.S. Pat. Nos. 4,380,635, 4,133,814 and 4,418,068, the disclosures of which are herein incorporated by reference. Compounds of formula VIII are known in the art and are generally commercially available or are prepared by methods well known in the art from readily available starting materials.

Compounds of formula IX may be prepared from compounds of formula V. For example, a compound of formula V may be acylated with a compound of formula VI to provide the compounds of formula VII. The Y group in compounds of formula VII is then displaced with a secondary amine of formula VIII to provide the compounds of formula IX. The overall process of the present invention is as depicted in Scheme 1 where $R^5$, $R^6$, $R^7$, $R^8$, and Y are as defined, supra.

Scheme 1

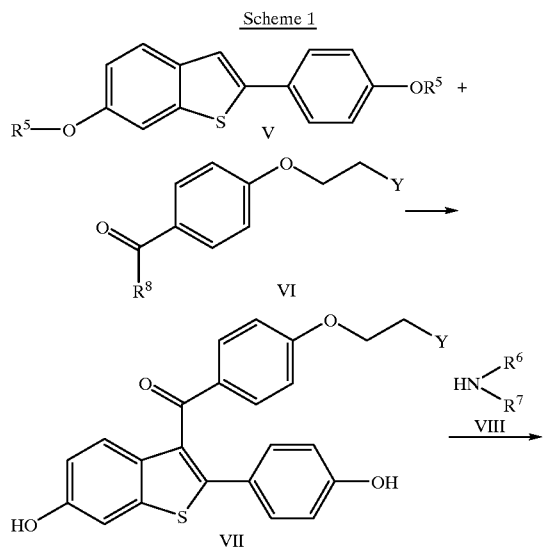

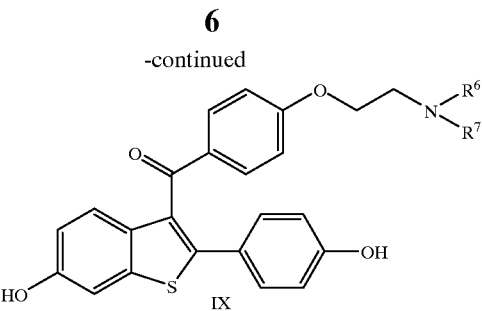

Compounds of formula IX may be prepared from compounds of formula V. For example, a compound of formula VI may be added to a compound of formula V, dissolved or suspended in a suitable solvent, in the presence of a boron trihalide. Suitable solvents include chlorobenzene, carbon tetrachloride, methylene chloride, chloroform, mixtures thereof, and the like. 1,2 Dichloroethane is typically the preferred solvent. The preferred boron trihalide is typically boron trichloride. The compound of formula V is typically employed in slight molar excess. For example, a 1.05 to 1.25 molar excess, relative to the compound of formula VI, is generally employed. A 1.1 molar excess is preferred. The boron trihalide is typically employed in a substantial molar excess. For example, a 4 to 8 molar excess, relative to the compounds of formula VI, is generally employed. A 6 molar excess is preferred. The reaction is typically carried out by adding the boron trihalide in 2 equal portions to a solution containing a compound of formula V and a compound of formula VI. The first portion is generally added at 0–5° C. and the resulting mixture allowed to stir for about 7 hours at 0–5° C. The second addition of trihalide is generally accompanied by the warming of the reaction to about 30° C. and stirring for about 16 hours.

Compounds of formula IX may be prepared from compounds of formula VII and compounds of formula VIII. For example, a compound of formula VIII may be added to a compound of formula VII, dissolved or suspended in a suitable solvent in the presence of a catalytic amount of an iodide or bromide salt. Suitable solvents include methylene chloride, chloroform, acetonitrile, tetrahydrofuran, ethyl acetate, lower alcohols, mixtures thereof, and the like. Dimethylformamide is the preferred solvent. Suitable iodide or bromide salts include potassium sodium, or lithium salts. Potassium iodide is the preferred salt. The compound of formula VIII is generally employed in a substantial molar excess. For example, a 20 to 30 molar excess, relative to the compounds of formula VII is generally employed. A 25 molar excess is typically preferred. The reaction is generally performed at about 50° C. for about 18 hours.

Compounds of formula VI are prepared by methods well known in the art. For example, a 4-hydroxybenzoic acid or ester of formula X is reacted with a compound of formula XI followed by, when $R^8$ is not hydrogen, basic hydrolysis of the ester to the acid of formula XIIa. The acid group in compounds of formula XIIa is then converted to a Y group to provide the compounds of formula VI. This chemistry is depicted in Scheme 2 where $R^9$ is hydrogen or $C_1$–$C_4$ alkyl, and $R^8$ and Y are as defined, supra.

Scheme 2

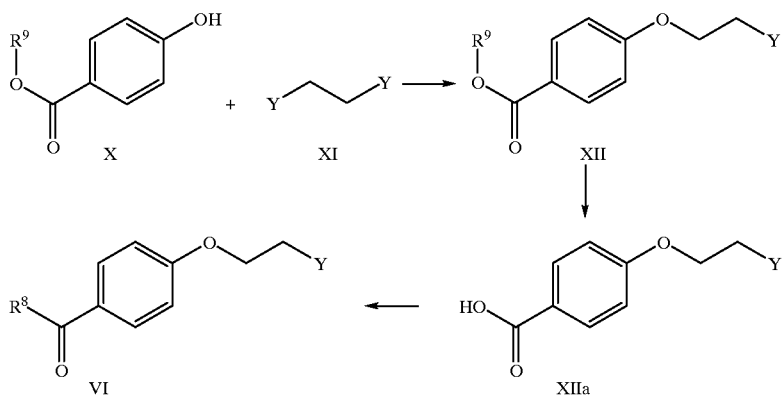

Compounds of formula XII are prepared by methods well known in the art. For example, a compound of formula X, dissolved or suspended in an suitable solvent, in the presence of a suitable base, is treated with a compound of formula XI. Suitable solvents include methylene chloride, tetrahydrofuran, lower alcohols, dimethyl sulfoxide, dimethylformamide, acetonitrile, mixtures thereof, and the like. Dimethylformamide or dimethylsulfoxide is the preferred solvent. Suitable bases include sodium, potassium, or cesium carbonate, and the like. Potassium carbonate is the preferred base. A preferred compound of formula XI is where Y is chloro at both positions. The base is generally employed in an substantial molar excess. For example, a 1.5 to 2.5 molar excess, relative to the compounds of formula X, is generally employed. A 2.0 molar excess is typically preferred. The compound of formula XI is typically employed in a substantial molar excess. For example, the reaction is preferably run with the compound of formula XI as a co-solvent. The reaction is preferably run at the reflux temperature of the solvent for about 12 hours.

The compounds of formula XIIa are obtained from compounds of formula XII by well known methods in the art. For example, a compound of formula XII, dissolved in a suitable solvent, may be treated with a suitable base. Suitable solvents include lower alcohols, tetrahydrofuran, dimethylformamide, acetonitrile, diethyl ether, mixtures thereof and the like. A mixture of water and methanol is the preferred solvent. Suitable bases include alkali earth hydroxides including potassium hydroxide, and the like. Sodium hydroxide is the preferred base. The base is typically employed in a slight molar excess. For example, a 1.1 to a 1.4 molar excess relative to the compound of formula XII is typically employed. A 1.2 molar excess is generally preferred. The reaction is preferably run at the reflux temperature of the solvent for about 1 hour.

Compounds of formula VI which have an acyl activating group ($R^8$) are prepared from compounds of formula XIIa by methods well known in the art. For example, when $R^8$ is to be chloro, a compound of formula XIIa, dissolved or suspended in a suitable solvent, may be treated with thionyl chloride. The remaining compounds of formula VI may be prepared by similarly well known methods in the art.

In general, the reactions of Schemes 1 and 2 are complete in about 15 minutes to 72 hours when conducted at a temperature range of from about 0° C. to about the reflux temperature of the given reaction mixture. The reaction solvent choices are not critical as long as the solvent employed is inert to the ongoing reaction and the reactants are sufficiently solubilized to effect the desired reaction. Once a reaction is complete, the intermediate compound may be isolated, if desired, by procedures known in the art. For example, the compound may be crystallized and then collected by filtration, or the reaction solvent may be removed by extraction, evaporation, or decantation. The intermediate may be further purified, if desired by common techniques such as recrystallization or chromatography over solid supports such as silica gel or alumina The compounds of formula V-XIIa are typically isolated before use in subsequent reactions.

The optimal time for performing the reactions of the invention can be determined by monitoring the progress of the reaction via conventional chromatographic techniques. Furthermore, it is preferred to conduct the reactions of the invention under an inert atmosphere, such as, for example, argon or nitrogen.

The following Examples are provided to better elucidate the practice of the present invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

EXAMPLES

Preparation 1

4-(2-Chloroethoxy)benzoic acid methyl ester 4-hydroxybenzoic acid methyl ester (1.52 g, 10 mmol), anhydrous potassium carbonate (1.38 g, 10 mmol), 10 ml of dimethylsulfoxide, and 20 ml of 1,2-dichloroethane are combined and heated to reflux. HPLC shows the reaction is at equilibrium at about 1 hour. Therefore, another equivalent of potassium carbonate is added. After the second addition of potassium carbonate, the ratio of product to bis alkylated biproduct is greatly enhanced. The reaction mixture is cooled to room temperature and diluted with 30 ml of water. The mixture is stirred then the layers separated. The organic layer is back extracted with 20 ml of brine and then filtered through sodium sulfate. The filtrate is concentrated in vacuo at about 60° C. to a yellow green oil which solidifies on cooling. This crude product is redissolved in 12 ml of hot methanol and water is added (total of 6 ml) dropwise until crystals appear. The crystallization is allowed to continue for one hour with cooling. The precipitate is filtered and rinsed with 12 ml of 1:1 methanol:water. The filter cake is dried in vacuo at about room temperature to give 2.00 g of product. (93.5%). HPLC.

Preparation 2

4-(2-Chloroethoxy)benzoic acid methyl ester 4-hydroxybenzoic acid methyl ester (1.52 g, 10 mmol), anhydrous lithium carbonate (740 mg, 10 mmol), 15 ml of dimethylsulfoxide, and 15 ml of 1,2-dichloroethane are combined and heated to reflux. HPLC shows the reaction is at equilibrium at about 2 hours with a product to starting material ratio of 22.7:68.7.

Preparation 3

4-(2-Chloroethoxy)benzoic acid methyl ester 4-hydroxybenzoic acid methyl ester (1.52 g, 10 mmol), anhydrous cesium carbonate (3.26 g, 10 mmol), 5 ml of dimethylsulfoxide that is dried over 4A molecular sieve, and 15 ml 1,2-dichloroethane are combined and stirred at about room temperature. After 15 hours the mixture is heated to reflux and more cesium carbonate (about 1 more equivalent). HPLC shows the ratio of product to bis alkylated biproduct to starting material is 93.1:6.2: non-detectable. The reaction mixture is cooled to room temperature and diluted with 30 ml of water. The mixture is stirred then the layers separated. The aqueous layer is extracted with 15 ml of methylene chloride and then the combined organics are filtered through sodium sulfate. The filtrate is concentrated in vacuo at about 60° C. to a yellow green oil which solidifies on cooling to give 2.00 g of product. (94.8%). HPLC.

Preparation 4

4-(2-Chloroethoxy)benzoic acid methyl ester 4-hydroxybenzoic acid methyl ester (30.4 g, 200 mmol), anhydrous cesium carbonate (13.82 g, 100 mmol), 100 ml of dimethylformamide, and 400 ml 1,2-dichloroethane are combined and heated to reflux. Progress is monitored by HPLC and at the 1 and 5 hour marks an additional equivalent of potassium carbonate is added. At the 24 hour mark, and addition 0.5 equivalents of potassium carbonate is added. HPLC shows the ratio of product to bis alkylated biproduct to starting material is 93.7:4.2: non-detectable. The reaction mixture is cooled to room temperature and diluted with 500 ml of water. The mixture is stirred then the layers separated. The aqueous layer is extracted with 50 ml of 1,2 dichloroethane and then the combined organics are filtered through sodium sulfate. The filtrate is concentrated in vacuo at about 60° C. to a yellow green. The residue is taken up in 200 ml of methanol and water is added until a permanent cloudy point is reached (about 50 ml). Crystallization begins immediately and once the mixture becomes thick another 50 ml of water is added. This mixture is stirred for 30 minutes and filtered. The filter cake is rinsed with 100 ml of 1:1 methanol:water and dried in vacuo at room temperature to give 38.6 g of product. From the filtrate is obtained a second crop (2.48 g) to give 41.1 g of product. (97.6%). EA, UV, HPLC.

Preparation 5

4-(2-Chloroethoxy)benzoic acid

The 4-(2-Chloroethoxy)benzoic acid methyl ester (31.6 g, 150 mmol), 250 ml of methanol, and 36 ml of 5N sodium hydroxide are combined and heated to reflux. The solution becomes a clear pale yellow at about 50° C. After 1.25 hours of reflux, (67° C.) the solution is still clear. The progress of the reaction is checked by HPLC. 250 ml of water is then added and the temperature rose to 77° C. Concentrated hydrochloric acid is added dropwise to adjust the pH to 2.5 producing a white precipitate. The reaction is cooled to 19° C. for 2 hours and filtered. The filter cake is rinsed with 100 ml of chilled 1:1 methanol:water and dried in vacuo at 50° C. to give 28.03 g of crude product. The residue is stirred in 350 ml of boiling methanol and filtered through a large pre-heated Buchner funnel. The filtrate rapidly becomes cloudy and when the mixture returns to room temperature it is filtered. The filter cake is rinsed with 70 ml of methanol 5 times. To the filtrate is added 5N sodium hydroxide till the pH is adjusted to about 12. The pH is then adjusted back down to about 4 with acetic acid. The addition of 400 ml of water gives a heavy precipitate that is filtered. The filter cake is rinsed with 100 ml of 1:1 methanol:water and dried in vacuo at 50° C. to give 22.2 g of product. The filtrate is diluted with 300 ml of water and the pH is adjusted to 1 with hydrochloric acid. The resulting precipitate is collected by suction filtration and rinsed with 100 ml of 1:1 methanol:water and dried in vacuo at 50° C. to give 3.95 g of a white solid. The combined product is stirred in 520 ml of methanol as 45% potassium carbonate is added. After 55 ml of the basic solution is added the mostly dissolved mixture begins to precipitate. The addition of 120 ml of water and 120 ml of methanol gives a hazy solution. The layers are separated and the top layer is filtered. The pH of the filtrate is adjusted to 7 with acetic acid which causes a precipitation. The light amount of precipitate is filtered off. The filtrate is slowly adjusted to pH 4 with hydrochloric acid and then filtered. The filter cake is rinsed with 150 ml of 1:1 methanol:water to give 21.48 g of product. (71.4%). $^1$H NMR, HPLC.

Preparation 6

4-(2-Chloroethoxy)benzoyl chloride

In a 250-ml flask are combined 4-(2-chloroethoxy) benzoic acid (2.58 g, 12.9 mmol), dimethylformamide (0.2 ml) and 1,2-dichloroethane (50 ml). Oxalyl chloride (1.35 ml) is added dropwise and the reaction mixture stirred overnight at room temperature. The reaction becomes homogeneous after stirring several hours. After an overnight stir, the solvent is evaporated to dryness, and the solid product is redissolved in 1,2-dichloroethane (2×50 mL) and evaporated. The product is used as is in subsequent reactions.

Example 1

2-(4-Hydroxyphenyl)-3-(4-[2-chloroethyl]benzoyl)-6-hydroxybenzo[b]thiophene

In a 100-ml three-necked flask fitted with mechanical agitator and 2 glass stoppers are combined 4-(2-chloroethoxy)benzoyl chloride, 2-(4-methoxyphenyl)-6-methoxybenzo[b]thiophene (3.17 g, 11.73 mmol, and 50 ml of 1,2-dichloroethane. The mixture is cooled to 0–5° C. Boron trichloride (3.0 ml, 35.2 mmol) is added to the mixture in one portion. The mixture is stirred for 7 h at 0–5° C. A second addition of $BCl_3$ (3.0 ml, 35.2 mmol) is added and the reaction mixture is warmed to 30° C. and stirred overnight (about 16 hours) at this temperature. The reaction mixture is quenched by the slow addition of 50 ml methanol. The mixture is concentrated in vacuo to give a crude residue. Purification by flash chromatography (50% ethyl acetate/hexane) afforded 4.38 g (88%) of 343033 as a bright yellow powder: mp 146–148° C.; $^1$H NMR (300.1 MHz, DMSO-$d_6$) δ 3.91 (m, 2H), 4.26 (m, 2H), 6.68 (d, J=8.7 Hz, 2H), 6.86 (dd, J=2.2 and 8.8 Hz, 1 H), 6.93 (d, J=8.9 Hz, 2H), 7.17 (d, J=8.7 Hz, 2H), 7.27 (d, J=8.8 Hz, 1H), 7.35 (d, J=2.2 Hz, 1H), 7.67 ( d, J=8.9 Hz, 2H), 9.75 (s, 1H), 9.80 (s, 1H); $^{13}$C NMR (75.5 MHz, DMSO-$d_6$) d 42.8, 68.2, 107.1, 114.5, , 115.2, 115.7, 123.3, 123.8, 129.6, 129.7, 130.1, 131.8, 132.3, 139.3, 140.6, 155.4, 157.8, 162.2, 192.5.

Example 2

2-(4-Methoxyphenyl)-3-(4-(2-piperidinoethoxy)
benzoyl)-6-hydroxybenzo[b]
thiophene.hydrochloride In a 50 ml three-neck flask fitted, $N_2$ purging inlet and thermometer are combined 2-(4-hydroxyphenyl)-3-(4-[2-chloroethyl]benzoyl)-6-hydroxybenzo[b]thiophene (885 mg, 2.0 mmol), potassium iodide (365 mg, 2.2 mmol), piperidine (5.0 ml, 50 mmol) and dimethylformamide (5 ml). The solution is heated to 50° C. and stirred for 18 h. HPLC analysis indicated that the reaction is complete. The mixture is cooled and diluted with ethyl acetate (50 ml). The solution is washed with 3% Aqueous sodium bicarbonate (3×50 ml), dried over sodium sulfate, and concentrated in vacuo to give 1.3 g of a crude orange residue. The residue is dissolved in methanol (5 ml) and concentrated hydrochloric acid (3 drops) is added. The mixture is seeded with a pure sample of 2-(4-methoxyphenyl)-3-(4-(2-piperidinoethoxy) benzoyl)-6-hydroxybenzo[b]thiophene.hydrochloride and stirred at ambient temperature for 66 hours. The resulting slurry is filtered, washed with cold methanol, and dried in vacuo at 40° C. to give 798 mg (78%) of product as a light yellow solid: m.p. 254–256° C. (Lit. 258° C.); $^1$H NMR (300.1 MHz, DMSO-$d_6$) δ 1.32 (m, 1H), 1.65 (m, 1H), 1.73 (br s, 4H), 2.93 (m, 2H), 3.40 (m, 4H), 3.62 (br s, 1H), 4.45 (m, 2H), 6.68 (d, 2H), 6.83 (dd, 1H), 6.94 (d, 2H), 7.13 (d, 2H), 7.24 (d, 1H), 7.37 (d, 1H), 7.58 (d, 2H), 9.88 (br s, 1H), 10.46 (br s, 1H); $^{13}$C NMR (75.5 MHz, DMSO-$d_6$) d 23.9, 25.5, 25.6, 54.3, 54.4, 57.1, 65.9, 107.1, 114.5, 115.2, 115.7, 123.3, 123.6, 129.63, 129.64, 129.7, 131.8, 132.2, 139.2, 140.3, 155.6, 158.0, 162.8, 192.6.

We claim:
1. A compound of formula VII

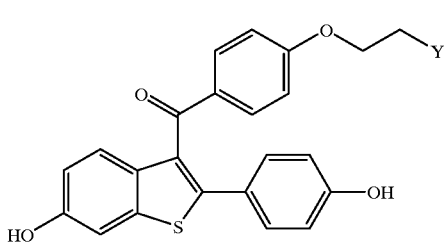

wherein Y is chloro, bromo, iodo, or $SO_2R^9$; and
$R^9$ is $C_1$–$C_4$ alkyl, trifluoromethyl, trichloromethyl, phenyl, p-tolyl, p-anisyl, or mono- or di(halo or nitro)phenyl.
2. A compound of claim 1 wherein Y is $SO_2R^9$.
3. A compound according to claim 1 wherein Y is chloro.

4. A process for preparing a compound of formula VII

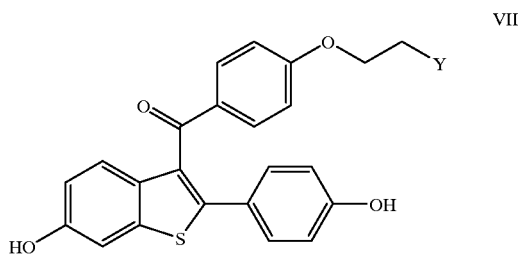

wherein Y is chloro, bromo, iodo, or $SO_2R^9$, and $R^9$ is $C_1$–$C_4$ alkyl, trifluoromethyl, trichloromethyl, phenyl, p-tolyl, p-anisyl, or mono- or di(halo or nitro)phenyl;
which comprises reacting a compound of formula V

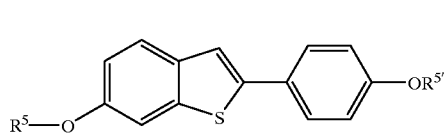

wherein $R^5$ and $R^{5'}$ are independently hydroxy protecting groups;
with a compound of formula VI

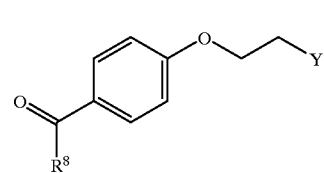

wherein $R^8$ is an acyl activating group; in the presence of a boron trihalide.
5. A process according to claim 4 wherein said boron trihalide is boron trichloride.
6. A process according to claim 4 wherein $R^8$ and Y are both chloro.
7. A process according to claim 3 which further comprises reacting a compound of formula VII

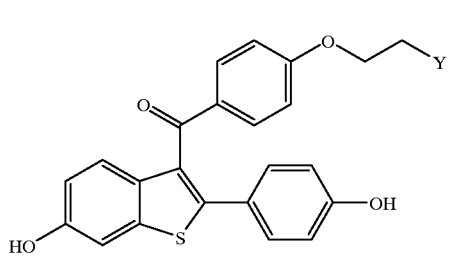

with a compound of formula VIII

wherein $R^6$ and $R^7$ are independently $C_1$–$C_4$ alkyl, or combine together with the nitrogen to which they are attached a to form piperidinyl, pyrrolidinyl, methylpyrrolidinyl, dimethylpyrrolidinyl, morpholino, or 1-hexamethyleneimino ring; to produce a compound of formula IX

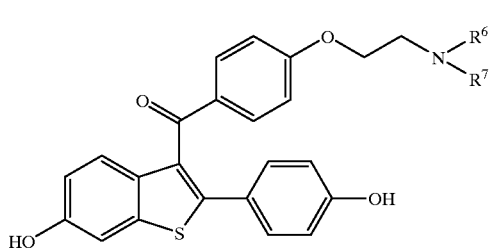

IX or a pharmaceutically acceptable salt or solvate thereof.

8. A process according to claim 7 wherein said boron trihalide is boron trichloride.

9. A process according to claim 8 wherein $R^8$ and Y are both chloro.

10. A process according to claim 8 wherein said compound of formula VIII is a compound wherein $R^6$ and $R^7$ combine with the nitrogen atom to which they are attached to form a piperidinyl ring.

11. A process according to claim 7 wherein said salt thereof is the hydrochloride salt.

* * * * *